US00PP36878P2

(12) United States Plant Patent
Klein

(10) Patent No.: US PP36,878 P2
(45) Date of Patent: Aug. 5, 2025

(54) ***TRIFOLIUM* PLANT NAMED 'Coretta Clover'**

(50) Latin Name: *Trifolium repens*
Varietal Denomination: Coretta Clover

(71) Applicant: Jeffrey Klein, Shaker Heights, OH (US)

(72) Inventor: Jeffrey Klein, Shaker Heights, OH (US)

( * ) Notice: Subject to any disclaimer, the term of this patent is extended or adjusted under 35 U.S.C. 154(b) by 0 days.

(21) Appl. No.: 18/942,836

(22) Filed: Nov. 11, 2024

(51) Int. Cl.
*A01H 6/00* (2018.01)
*A01H 5/02* (2018.01)

(52) U.S. Cl.
USPC ..... Plt./388

(58) Field of Classification Search
USPC ..... Plt./263.1, 388
CPC ..... A01H 6/00; A01H 5/02
See application file for complete search history.

*Primary Examiner* — Keith O. Robinson

(57) ABSTRACT

A new and distinct strain of *Trifolium repens* (white clover) named 'Coretta Clover' is disclosed, characterized by its consistent ability to produce a higher percentage of compound leaves with four and five leaflets, in combination with its leaf shape. This unique strain exhibits a propensity for approximately 0.5% to 5% of its compound leaves to be four-leaf clovers and 0.075% to 0.75% to be five-leaf clovers, a significant deviation from the typical three-leaflet morphology common to the species. The distinctive traits are stable and reproducible in asexual propagation, providing a novel variety of *Trifolium repens* that combines aesthetic appeal with rarity, while maintaining the general hardiness and adaptability of the species. The strain's unique phenotypic traits are of particular interest for ornamental, agricultural, artistic, cultural, and commercial applications.

6 Drawing Sheets

Latin name of the genus and species: *Trifolium repens*.
Variety denomination: 'Coretta Clover'.

CROSS-REFERENCE TO RELATED APPLICATIONS

Not applicable.

STATEMENT REGARDING FEDERALLY SPONSORED RESEARCH OR DEVELOPMENT

Not applicable.

BACKGROUND OF THE INVENTION

The present invention relates to a new and distinct variety of *Trifolium repens*, commonly known as white clover, which has been developed with a unique propensity for producing four-leaf and five-leaf clovers, in combination with leaf shapes being oval to obovate, with a slightly indented tip (as represented in FIGS. 1-5). White clover is a widely grown perennial legume, known for its use in lawns, pastures, and as a cover crop due to its nitrogen-fixing properties.

Traditionally, *Trifolium repens* exhibits compound leaves with three leaflets. Occurrences of four-leaf clovers, although considered rare, have been sporadically observed in natural populations, often prized for their association with good luck. Even rarer are five-leaf clovers, which are less commonly noted. However, previous varieties of white clover have not demonstrated a stable or reproducible trait of generating four-leaf and five-leaf clovers.

The new variety described herein has been selected for its increased and consistent frequency of producing four-leaf and five-leaf clovers in combination with its leaf shape. These characteristics, which have been stabilized through multiple generations of asexual propagation, make this new variety unique and valuable for ornamental, agricultural, artistic, cultural, and commercial purposes. The parentage of this new variety is unknown, as it was isolated from a naturally occurring population in the wild.

While various wild-type and cultivated varieties of *Trifolium repens* are known, they predominantly exhibit trifoliate leaf structures, with the appearance of four- or five-leaf clovers being infrequent, random, and not reliably heritable. The claimed variety of *Trifolium repens* is distinct from the species and known commercial or wild-type cultivars in that it consistently produces a substantially higher proportion of leaflets with four or five leaflets. To the best of Applicant's knowledge, no existing variety of *Trifolium repens* exhibits the stable and reproducible trait of producing four-and five-leaf clovers at the elevated frequencies observed in the claimed variety. This claimed variety is distinguishable from known white clover plants by its consistent production of 0.5% to 5% of four-leaf clovers and 0.075% to 0.75% of five-leaf clovers, observed across multiple generations of asexual propagation. This frequency and stability of multi-leaflet morphology have not been documented in prior varieties, rendering the claimed plant, as described by the combination of characteristics disclosed herein, as both novel and distinct within the species.

BRIEF SUMMARY OF THE INVENTION

The present invention relates to a new and distinct variety of *Trifolium repens*, which is characterized by its ability to produce four-leaf and five-leaf clovers at a higher-than-typical rate, in combination with its leaf shape. Specifically, 0.5% to 5% of the compound leaves of this new variety develop four leaflets, and 0.075% to 0.75% develop five leaflets. These traits are stable and reproducible in asexual propagation. This new variety retains the hardy, low-growing, nitrogen-fixing properties of common white clover while offering a visually striking and unique appearance. The new variety is of interest for use in ornamental gardens, pasture enhancements, lawns, art, works of cultural significance, and novelty applications in consumer products.

BRIEF DESCRIPTION OF THE FIGURES

FIG. 1: A close-up photograph showing the front of a typical three-leaflet form of the new variety. The age of this asexually reproduced progeny of 'Coretta Clover' is approximately four months.

FIG. 2: A close-up photograph showing the front of a typical four-leaflet form of the new variety. The age of this asexually reproduced progeny of 'Coretta Clover' is approximately four months.

FIG. 3: A close-up photograph showing the back of a typical four-leaflet form of the new variety. The age of this asexually reproduced progeny of 'Coretta Clover' is approximately four months.

FIG. 4: A close-up photograph showing the front of a typical five-leaflet form of the new variety. The age of this asexually reproduced progeny of 'Coretta Clover' is approximately four months.

FIG. 5: A close-up photograph showing the back of a typical five-leaflet form of the new variety. The age of this asexually reproduced progeny of 'Coretta Clover' is approximately four months.

FIG. 6: A diagram illustrating the frequency of distribution of three-, four-, and five-leaflet compound leaves in a representative population of the new variety. The age of this asexually reproduced progeny of 'Coretta Clover' is approximately four months.

DETAILED BOTANICAL DESCRIPTION

The following detailed description sets forth the distinctive characteristics of this new variety of *Trifolium repens*. The data was collected from plants grown in Cleveland, OH under indoor greenhouse conditions, and the observations represent averages from multiple asexually propagated plants. The initial selection date of 'Coretta Clover' was Jul. 1, 2023, and the plant was approximately 16 months old at the time of submitting this detailed description.

Variety name: 'Coretta Clover'.

Genus and species: *Trifolium repens*.

Parentage: The new variety is derived from selective breeding of naturally occurring variants of *Trifolium repens* that exhibited the four-leaf trait, followed by stabilization of the trait through asexual propagation.

Propagation method: The new variety has been consistently propagated asexually via stolons and rhizomes. All subsequent generations have maintained the unique characteristics of the parent plant.

Growth habit:

*Plant form*.—Low-growing, mat-forming perennial.

*Plant size*.—The plant exhibits a prostrate to low-mounding growth habit, with an average height of approximately 4 to 12 cm from the soil surface to the top of the foliage. Under typical field conditions, mature plants form spreading mats or clumps with a diameter ranging from 20 to 50 cm, though spreading can extend further through stolon development over time.

*Growth rate*.—Moderate to vigorous, depending on environmental conditions.

*Branching habit*.—The plant exhibits a prostrate, stoloniferous growth habit, with horizontal stems (stolons) that extend along the soil surface and root at the nodes. Each stolon gives rise to new leaf clusters and inflorescences at regularly spaced intervals, allowing the plant to form spreading mats. The plant does not produce upright woody branches; instead, vegetative propagation occurs primarily through branching stolons.

*Root system*.—Fibrous, shallow.

Leaf characteristics:

*Leaf shape*.—Compound leaves with 3, 4, or 5 leaflets.

*Leaflet shape*.—Oval to obovate, with a slightly marginate apex. The margins are smooth (entire) and unlobed. Leaf surface exhibits a moderate luster, with the upper surface being semi-glossy and the lower surface matte. Venation is pinnate, with a central midrib and secondary veins branching outward in a reticulate pattern (as represented in FIGS. 1-5).

*Leaflet size*.—20-30 mm in length and width for typical three-leaflet, four-leaflet, and five-leaflet forms. Individual leaves are 10-15 mm in length and 7-10 mm in width for typical three-leaflet, four-leaflet, and five-leaflet forms.

*Leaflet color*.—Bright green (RHS Green Group 135C) with medium prominence white (RHS White Group NN155D) crescent markings at the base of each leaflet. Color references are made to The Royal Horticultural Society Colour Chart (R.H.S.), 2007 edition, except where general color terms of ordinary significance are used.

*Leaflet texture*.—Slightly glossy with a smooth surface.

*Leaf frequency*.—

*Three-leaflet*.—~97%.

*Four-leaflet*.—0.5% to 5%.

*Five-leaflet*.—0.075% to 0.75%.

Flower characteristics:

*Petiole*.—Slender, typically measuring 2.5 to 5.0 cm in length and approximately 0.5 to 1.0 mm in diameter. It is cylindrical in shape with a smooth surface texture and is glabrous. The petiole color is green (RHS Green Group 137C).

*Inflorescence*.—Globose clusters of small, white flowers. The flower color corresponds to RHS White Group 155A, occasionally exhibiting slight cream or pinkish tones as the flowers age, in which case aligning with RHS White Group 155B or 155C.

*Flower size*.—Each floret measures approximately 6-10 mm in length and 2-4 mm in width. Each inflorescence measures approximately 1.5-2.5 cm in diameter and 1-2 cm in height.

*Floret flowering period*.—Spring to early summer.

*Flowering habit*.—The plant exhibits an indeterminate and continuous flowering habit during spring to early summer. Inflorescences are borne singly on long peduncles that arise from the leaf axils, with moderate to abundant flowering observed in full sun.

*Flower fragrance and longevity*.—The flowers are lightly fragrant, with a mild, sweet scent that may be perceptible at close range. Individual inflorescences persist for approximately 5 to 7 days under normal field conditions, with flower color and structure gradually fading as the florets mature and senesce.

The plant produces successive inflorescences throughout the blooming season.

*Flower buds*.—The flower buds are narrow and elongated, ovate to slightly lanceolate in shape, measuring approximately 5 to 7 mm in length and 1.5 to 2.5 mm in diameter prior to anthesis. Buds are initially green (RHS Green Group 143C), with the upper portion gradually transitioning to white (RHS White Group 155A) or light pink (RHS Red-Purple Group 62D) as the corollas develop and prepare to open. Buds are borne singly on slender pedicels within the developing globose inflorescence.

*Petals*.—Each floret consists of five petals arranged in a papilionaceous (pea-like) configuration: a single broad upper petal (standard), two lateral petals (wings), and two fused lower petals (keel) that enclose the reproductive structures. The standard petal is broadly ovate to obovate in shape, measuring approximately 6 to 8 mm in length and 3 to 5 mm in width. The wings and keel are narrower, each measuring approximately 4 to 6 mm in length and 1.5 to 3 mm in width. Petal apices are rounded to slightly emarginate; margins are entire and smooth. Petal texture is delicate and membranous, with a slightly glabrous (non-hairy), soft surface. Petal surfaces exhibit a uniform coloration when fresh, typically white (RHS White Group 155A), occasionally showing faint pink tinges near the base (RHS Red-Purple Group 62D) as the florets mature.

*Sepals*.—Each floret is subtended by a calyx composed of five sepals that are fused at the base into a narrow tubular structure with five short, triangular lobes. The full calyx measures approximately 4 to 6 mm in length and 1.5 to 2.5 mm in diameter at the widest point. Sepal lobes are narrowly triangular to lanceolate in shape, with acute apices and entire margins. The surface texture is slightly pubescent (sparsely hairy), particularly along the lobes and calyx ridges. The color of the sepals is medium green (RHS Green Group 137C), occasionally showing faint purple tinges near the tips (RHS Greyed-Purple Group 183B) in high light conditions or as florets mature.

*Peduncles and pedicels*.—The inflorescences are borne singly on slender, erect peduncles that arise from the leaf axils. Each peduncle measures approximately 5 to 15 cm in length and 0.5 to 1.0 mm in diameter. Peduncles are cylindrical, smooth, and glabrous, with a firm but flexible texture. The color of the peduncle is green (RHS Green Group 137C). Individual florets are attached to the inflorescence head by short pedicels measuring approximately 1.0 to 1.5 mm in length. Pedicels are fine, glabrous, and similar in coloration to the peduncle.

*Seeds and fruit*.—To date, the claimed plant has been reproduced exclusively through asexual propagation, and no fruit or seed has been produced or observed. As a result, no data regarding the length, diameter, texture, or color of the seeds or fruits is available.

*Stamens, filaments, and anthers*.—Each floret of the claimed plant typically contains ten stamens. As is characteristic of *Trifolium repens* and other members of the Fabaceae family, the stamens are diadelphous — nine stamens are fused into a sheath and one stamen remains free. The filaments are slender and measure approximately 3.0 to 5.0 mm in length. Filament color ranges from white to pale green (RHS White Group 155D to Green Group 138D). The anthers are oblong in shape, measuring approximately 0.5 to 1.0 mm in length. Anther color is pale yellow when immature (RHS Yellow Group 4D), maturing to medium yellow at anthesis (RHS Yellow Group 8C).

*Pistil*.—The pistil, comprising a slender style terminating in a small, capitate stigma, typically measures approximately 3 to 5 mm in total length, consistent with the overall diminutive size of the floret.

*Style*.—The style is slender and glabrous, measuring approximately 2.5 to 4.0 mm in length. It has a smooth texture and is light green to pale yellow in color (RHS Green-Yellow Group 1D to Yellow Group 4D), terminating in a small, capitate stigma.

*Stigma*.—The stigma is small and capitate (rounded at the tip), positioned at the apex of the style. It is light green to pale yellow in color (RHS Yellow-Green Group 145D to Yellow Group 4D), with a smooth, glistening surface indicative of receptivity during anthesis.

*Ovary*.—The ovary is small, glabrous, and light green in color (RHS Green Group 138D), consistent with typical floral morphology in *Trifolium repens*. It is located at the base of the style and partially enclosed by the fused calyx.

*Pollen*.—The claimed plant produces a moderate to abundant quantity of pollen. Pollen is fine and powdery in texture and is light yellow in color (RHS Yellow Group 8D).

Disease resistance: The new variety exhibits similar resistance to common clover diseases (such as powdery mildew caused by *Erysiphe trifolii* and root rot caused by *Pythium ultimum*) as typical *Trifolium repens* varieties.

Environmental adaptation: This variety is well-suited for temperate climates and can be used in both pasture and lawn settings. It exhibits tolerance to moderate drought conditions and prefers well-drained, fertile soils.

The invention claimed is:

1. A new and distinct cultivar of *Trifolium repens* plant named 'Coretta Clover' as herein shown and described.

* * * * *

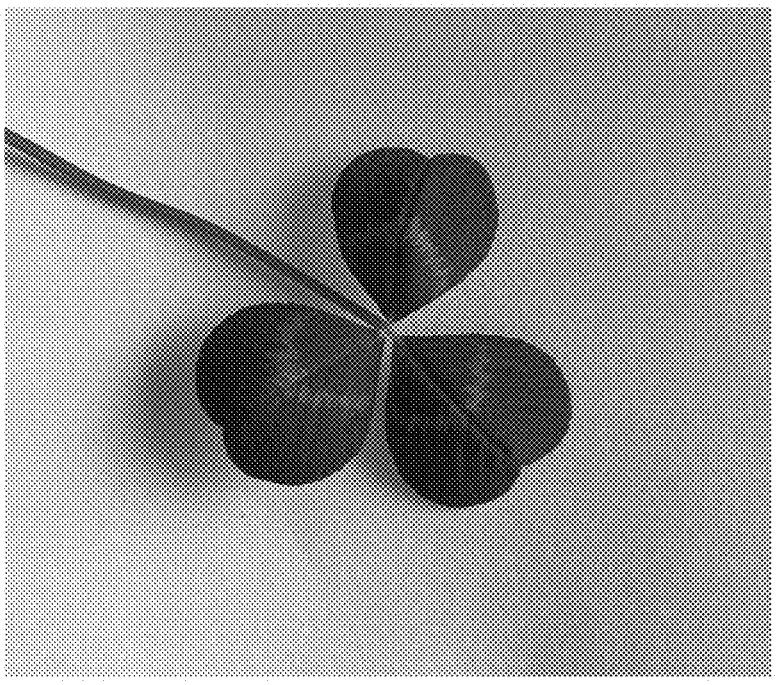
*FIG. 1: A close-up photograph showing the front of a typical three-leaflet form of the new variety.*

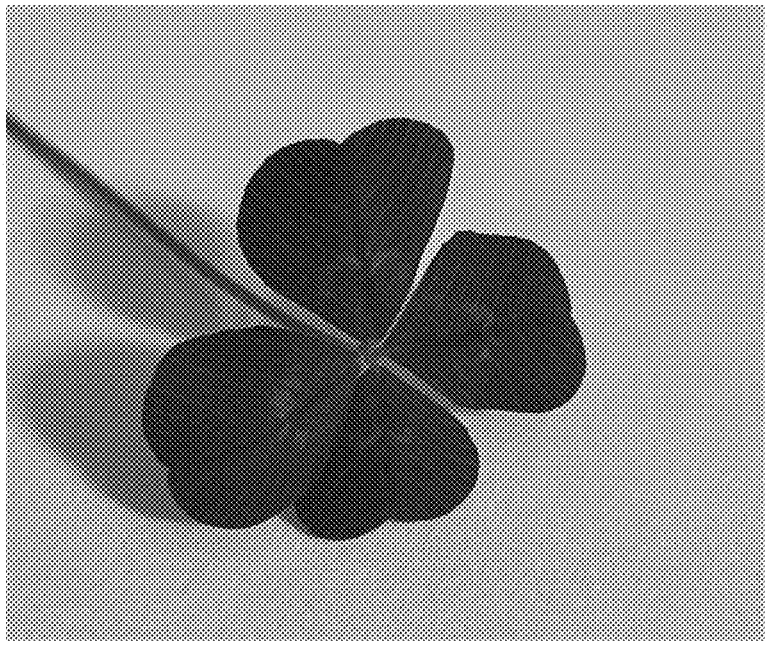
*FIG. 2: A close-up photograph showing the front of a typical four-leaflet form of the new variety.*

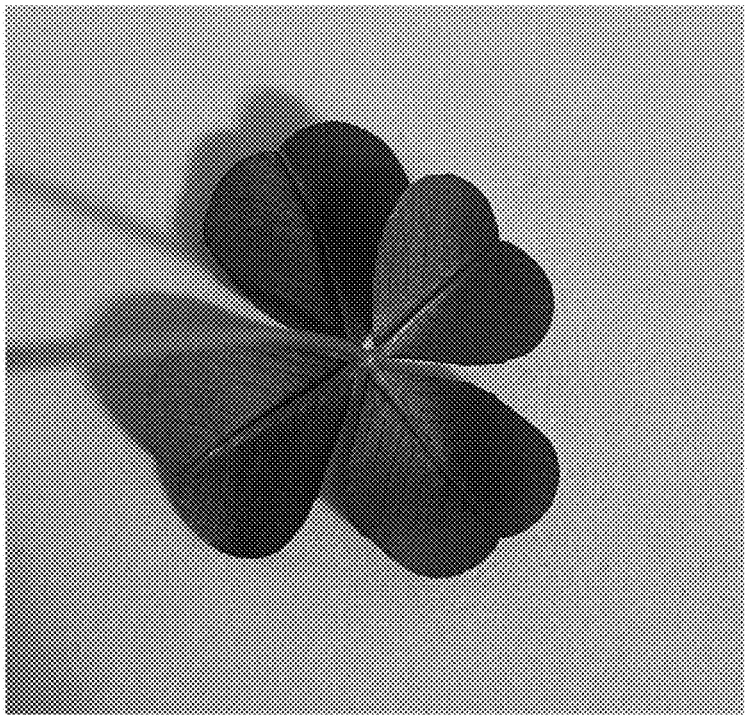
*FIG. 3: A close-up photograph showing the back of a typical four-leaflet form of the new variety.*

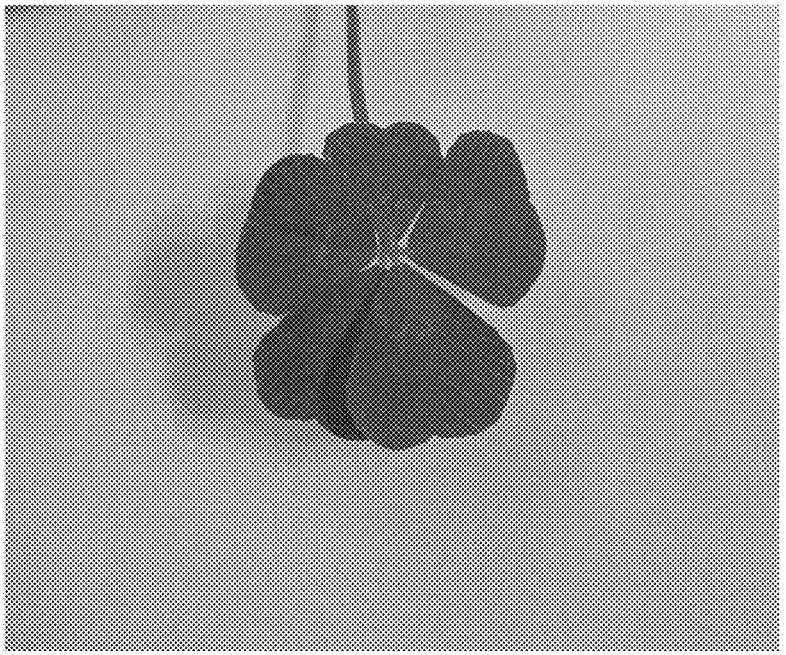
*FIG. 4: A close-up photograph showing the front of a typical five-leaflet form of the new variety.*

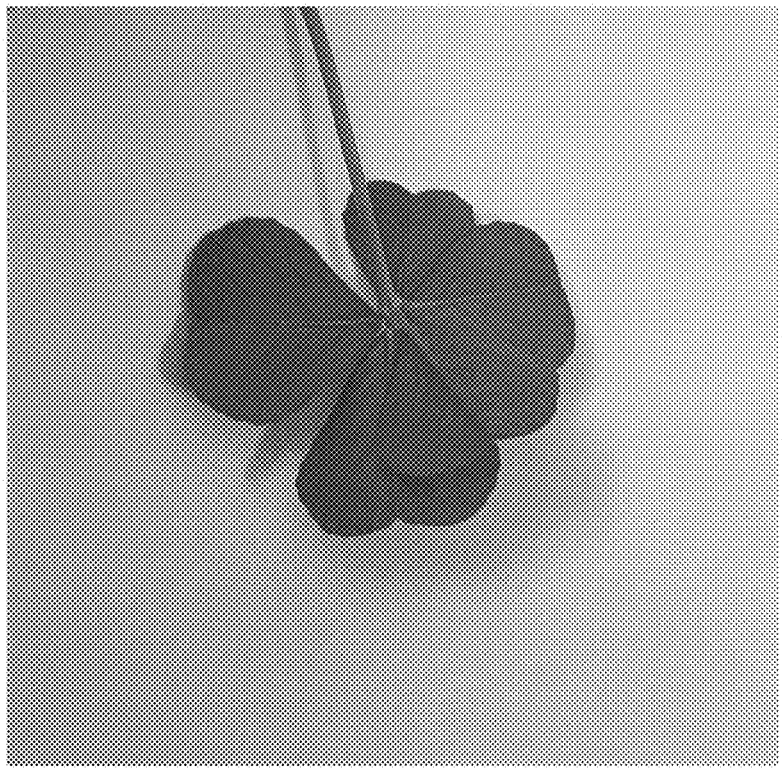
*FIG. 5: A close-up photograph showing the back of a typical five-leaflet form of the new variety.*

| | Total number counted | Frequency |
|---|---|---|
| Five-leaf clovers | 2 | 0.66% |
| Four-leaf clovers | 7 | 2.33% |
| Three-leaf clovers | 292 | 97.3% |

*FIG. 6: A diagram illustrating the frequency of distribution of three-, four-, and five-leaflet compound leaves in a representative population of the new variety.*